United States Patent
Kavusi et al.

(10) Patent No.: US 10,191,047 B2
(45) Date of Patent: Jan. 29, 2019

(54) SENSOR INTEGRATION IN LATERAL FLOW IMMUNOASSAYS AND ITS APPLICATIONS

(71) Applicant: Robert Bosch GmbH, Stuttgart (DE)

(72) Inventors: Sam Kavusi, Menlo Park, CA (US); Frederik Kotz, Karlsruhe (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/902,632

(22) Filed: Feb. 22, 2018

(65) Prior Publication Data
US 2018/0224446 A1 Aug. 9, 2018

Related U.S. Application Data

(62) Division of application No. 13/658,614, filed on Oct. 23, 2012, now Pat. No. 9,939,438.

(51) Int. Cl.
*G01N 33/543* (2006.01)
*G01N 33/561* (2006.01)

(52) U.S. Cl.
CPC ..... *G01N 33/561* (2013.01); *G01N 33/54366* (2013.01)

(58) Field of Classification Search
None
See application file for complete search history.

(56) References Cited

U.S. PATENT DOCUMENTS

| | | |
|---|---|---|
| 2005/0109637 A1 | 5/2005 | Iyengar et al. |
| 2005/0227275 A1 | 10/2005 | Jung et al. |
| 2009/0093968 A1 | 4/2009 | Kawamata et al. |
| 2010/0294660 A1 | 11/2010 | Wang et al. |
| 2012/0037513 A1 | 2/2012 | Lindemann |
| 2014/0274754 A1 | 9/2014 | Johnson et al. |

FOREIGN PATENT DOCUMENTS

| | | |
|---|---|---|
| CN | 101509924 | 8/2009 |
| JP | 2003-161733 | 6/2003 |
| JP | 2008-541017 | 11/2008 |
| JP | 200947590 | 3/2009 |
| JP | 20100522323 | 7/2010 |
| JP | 2010530534 | 9/2010 |
| WO | 02/10754 | 2/2002 |
| WO | 2005/051295 | 6/2005 |
| WO | 2006/119203 | 11/2006 |
| WO | 2007/007849 | 1/2007 |
| WO | 2008/115044 | 9/2008 |

(Continued)

OTHER PUBLICATIONS

Liu et al., Disposable Electrochemical Immunosensor Diagnosis Device Based on Nanoparticle Probe and Immunochromatographic Strip, Anal. Chem., 79, pp. 7644-7653, Published online on Sep. 19, 2007. (Year: 2007).*

(Continued)

*Primary Examiner* — Rebecca L Martinez
(74) *Attorney, Agent, or Firm* — Gerard Messina

(57) ABSTRACT

Lateral flow immunoassay devices for determining the concentration of an analyte in a sample and methods for measuring analyte concentration in sample using such lateral flow immunoassay devices.

18 Claims, 5 Drawing Sheets

(56) References Cited

FOREIGN PATENT DOCUMENTS

WO  2008/155579  12/2008
WO  2010/085271   7/2010

OTHER PUBLICATIONS

Jolke Perelaer et al., "Inkjet-printed silver tracks: low temperature curing and thermal stability investigation", Journal of Materials Chemistry (2008), vol. 18, pp. 3209-3215.
S. Wang et al., "Development of a colloidal gold-based lateral flow immunoassay for the rapid simultaneous detection of zearalenone and deoxynivalenol", Anal. Bioanal. Chemistry (2007).
"Lateral Flow Tests", Technote, Bangs Laboratories, Inc. (2008).

* cited by examiner

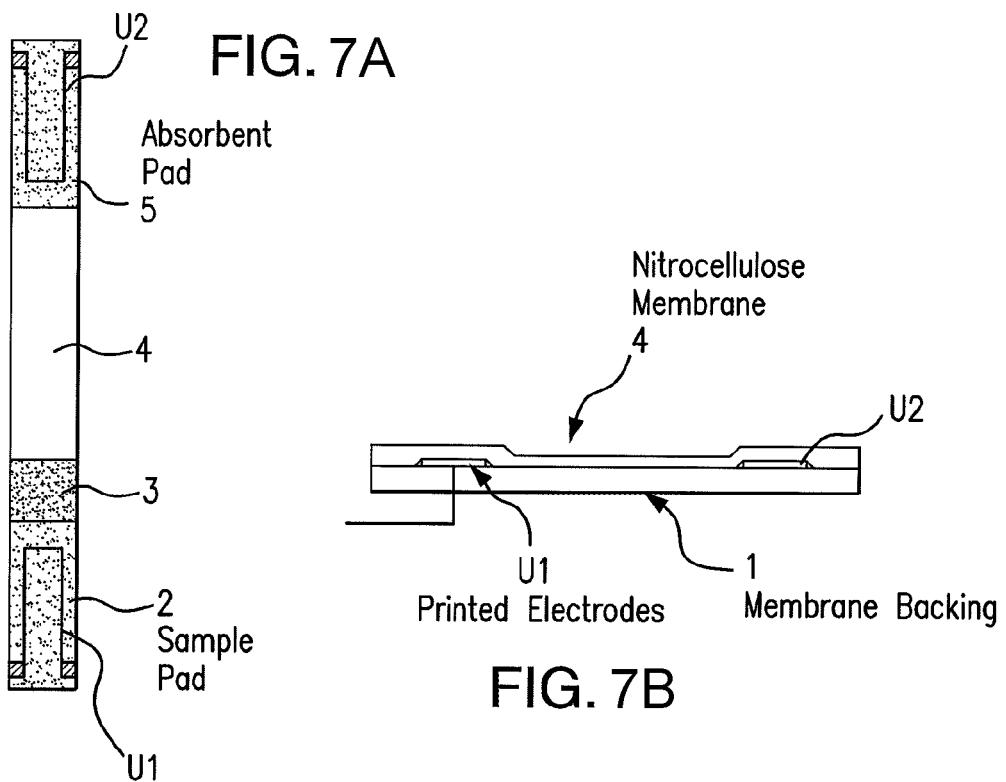
FIG. 7A
FIG. 7B
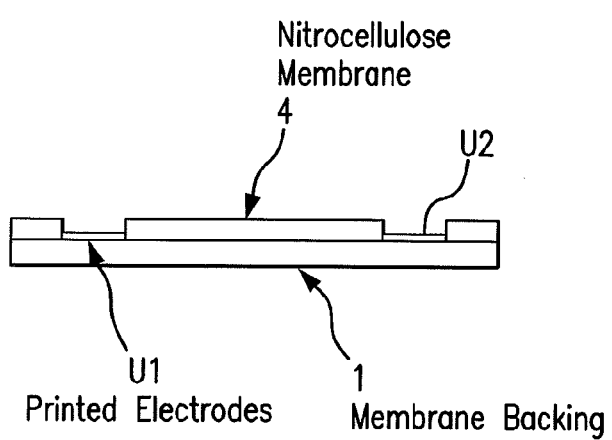
FIG. 7C

SENSOR INTEGRATION IN LATERAL FLOW IMMUNOASSAYS AND ITS APPLICATIONS

CROSS-REFERENCE TO RELATED APPLICATION

The present application is a divisional application of U.S. patent application Ser. No. 13/658,614, filed on Oct. 23, 2012, the content of which is hereby incorporated by reference herein in its entirety.

FIELD OF INVENTION

The invention relates to a device for Lateral Flow Immunoassays (LFIA's) as a biosensor, methods of improving such LFIA device, and using such LFIA device in a diagnostic method.

BACKGROUND INFORMATION

Recently there has been an increased interest in predictive, preventative, and particularly personalized medicine which requires diagnostic tests with higher fidelity, e.g., sensitivity and specificity. Lateral Flow Immunoassay (LFIA) devices incorporate such diagnostic test and is a well-established technology in Point-of-Care (POC) diagnostics. Low cost, relative ease of manufacture, long shelf life, and ease of use by the customer are some of the advantages that make LFIA's very attractive.

The basic principal of a Lateral Flow Immunoassay is shown in FIG. 1. During the early development of LFIA diagnostic devices, the main focus was primarily on qualitative systems which provide an easy yes or no answer. The best know qualitative lateral flow system is the pregnancy test.

Currently however, there is an increasing demand for more sensitive, quantitative and also multiplexing measurements which require the implementation of reader systems. As such, Lateral Flow Immunoassay Devices can be used in new markets and for new applications.

The capillary flow rate is very important for LFIA's because the effective concentration of an analyte in a sample decreases with the square of an increase in flow rate. For quantitative measurements of analytes this relationship is very important because the signal intensity directly correlates with the effective concentration. Thus, the flow speed of the sample across the analytical test line affects quantitative measurements for the analyte of interest. For example a sample viscosity change of 30%, within normal blood viscosity variation, will result in up to 70% signal variation.

The viscosity of different samples, for example blood samples, may vary significantly. The significant variation in viscosity of samples (and therefore the capillary flow rate) does not generally affect the performance of pregnancy tests; however, when a biomarker value, such as its concentration, is to be tested and compared to its previous values quantification of the analyte/biomarker is very important.

In LFIA's the flow of the sample through the membrane is driven by capillary forces. The pore size of the absorbent materials/membranes and the viscosity of the sample are two parameters that have a direct influence on the flow speed of the sample through the system. With respect to the flow speed/rate damage to the membrane of the LFIA during the manufacturing process will introduce multiple artifacts that adversely affect the flow behavior. For example, separation of the membrane from the backing (or adhesive tape) results in an unobstructed path for the sample to flow rapidly down the edge of the membrane. This will lead to a concave flow and artifacts in the measurement.

Printed electronics includes certain printing methods which allow the creation of circuits on a huge variety of substrates such as paper or textiles. Advantages of printed electronics are that they allow low-cost, high-volume, high-throughput production of electrical systems. Especially for small, inexpensive and disposable devices this technology can be very advantageous in improving reliability of quantitative diagnostic test using LFIA's. This makes printed electronics very attractive to the field of single use biosensors.

Jolke Perelaer et al., "Inkjet-printed silver tracks: low temperature curing and thermal stability investigation", *Journal of Materials Chemistry* (2008), vol. 18, pp 3209-3215, describe inkjet printing of ink at low temperature. The possibility to print low temperature curing materials increases the amount of usable material on which the electrodes can be printed (for example printing on temperature sensitive nitrocellulose membranes). Other printing methods such as roll to roll printing and stamping are also possible.

Some other key factors that affect the signal produced in a lateral flow test include temperature and ionic strength (including pH) of the solution. Including sensors and actuators that measure and influence such conditions is also important in reducing variations in the signal generated.

SUMMARY OF INVENTION

A lateral flow immunoassay device comprising at least one electrical sensor can measure one or more parameters which affect the signal intensity of an analyte of interest in a sample. An integrated printed electrical sensor in a lateral flow immunoassay device can measure such parameters which include for example the flow rate, flow shape, temperature or ionic concentration of the sample when flowing across the device.

In one embodiment there is provided a lateral flow immunoassay device for measuring an analyte having a solid support including absorbent material for providing capillary flow comprising:

a) a sample portion for receiving a sample;
b) a conjugate portion comprising conjugate particulate material;
b) a diagnostic portion comprising a binder for the analyte;
c) an absorbent portion of absorbent material for providing capillary flow; and
d) at least one electrical sensor, wherein the sample portion, conjugate portion, diagnostic portion, and absorbent portion are in capillary flow communication, whereby the sample flows across the binder in the diagnostic portion to provide contact between the sample and the binder.

The at least one electrical sensor in the lateral flow immunoassay device is connected to a processing unit for computing one or more parameters relating to the sample. The parameter(s) that are computed are those that affect the intensity of the signal from the bound labeled-analyte complex, thereby affecting the computation of the concentration of the analyte in the sample. For example such parameters of the analyte include the flow rate of the sample across the diagnostic portion, the flow shape of the sample across the diagnostic portion, the temperature of the sample at the diagnostic portion, the pH of the sample at the diagnostic portion, and the ionic concentration of the sample at the diagnostic portion.

In another embodiment there is provided a method of determining the concentration of an analyte in a sample comprising determining the analyte in the sample and a parameter of the sample in a lateral flow immunoassay device, wherein the lateral immunoassay device comprises a solid support including absorbent material for providing capillary flow comprising:

a) a sample portion for receiving a sample;
 b) a conjugate portion comprising conjugate particulate material;
 b) a diagnostic portion comprising a binder for the analyte;
 c) an absorbent portion of absorbent material for providing capillary flow; and
 d) at least one electrical sensor,
wherein the sample portion, conjugate portion, diagnostic portion, and absorbent portion are in capillary flow communication, whereby the sample flows across the binder in the diagnostic portion to provide contact between the sample and the binder.

The concentration of the analyte in the sample is computed by determining the signal intensity of the labeled-analyte bound to the diagnostic portion of the lateral flow immunoassay device and taking in consideration one or more of the parameters that were determined for the sample flowing across the diagnostic portion of the lateral flow immunoassay device.

BRIEF DESCRIPTION OF FIGURES

FIG. 7A: Schematic representation of alternative electrical sensor integration on a solid support of a later flow immunoassay device: a) the electrical sensor is on a portion of the solid support different from the diagnostic portion.

FIG. 7B: Schematic representation of alternative electrical sensor integration on a solid support of a later flow immunoassay device: electrical sensor integration is below the membrane of the diagnostic portion through a support layer/membrane.

FIG. 7C: Schematic representation of alternative electrical sensor integration on a solid support of a later flow immunoassay device: electrical sensor integration is through gaps in the membrane of the diagnostic portion of the solid support.

DETAILED DESCRIPTION

Figure 1:
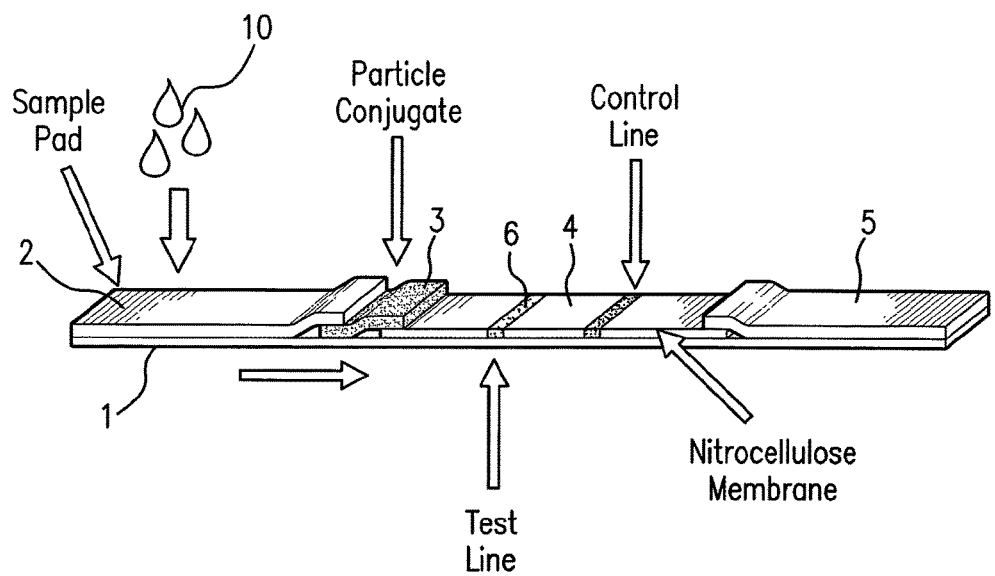
FIG. 1: A schematic representation of a lateral flow immunoassay device.

Electrical sensors can be integrated into Lateral Flow Immunoassay (LFIA) devices for determining parameters of a sample, which parameters affect the accuracy for measuring the concentration of an analyte of interest in such sample. Different kinds of printed electrical sensors that can be integrated into a Lateral Flow Immunoassay (flow speed sensor, flow shape sensor, temperature sensor) are provided. Nearly every printing process can be used to print these conductive electrodes for example screen-printing, gravure printing or inkjet-printing but also spraying or brushing techniques. The materials for these electrical sensors include for example silver, platinum, carbon, copper or gold inks or pastes.

Since some of the solvents of conductive materials can attack the membranes (especially nitrocellulose) used in the diagnostic portions of the LFIA, the electrodes can also be applied on different parts of the system (for e.g. bellow the nitrocellulose membrane on the backing-access through the backing). For example certain alternatives for integrating a printed electrode sensor in a LFIA device are shown in FIG. 7. These include printing of the electrode on a backing or support material below the membrane, wherein the electrode may be accessed through the backing or solid support material. As is shown for example in FIG. 7b wherein the electrodes could easily be connected through the backing. Alternatively, the electrodes are printed on the diagnostic portion (the diagnostic membrane) or in gaps of such diagnostic portion of the LFIA device. In another alternative, the electrodes are not printed electrodes but comprise non-printed electrodes applies to or through one or more of the various portions of the LFIA device.

As such there is provided a lateral flow immunoassay device for measuring an analyte having a solid support including absorbent material for providing capillary flow comprising:

a) a sample portion for receiving a sample;
 b) a conjugate portion comprising conjugate particulate material;
 b) a diagnostic portion comprising a binder for the analyte;
 c) an absorbent portion of absorbent material for providing capillary flow; and
 d) at least one electrical sensor,
wherein the sample portion, conjugate portion, diagnostic portion, and absorbent portion are in capillary flow communication, whereby the sample flows across the binder in the diagnostic portion to provide contact between the sample and the binder. Binding of the analyte in the sample (and the conjugate) to the binder, located on a test-line of the diagnostic portion, will result in a signal being generated at that location. The intensity of the signal being generated is an indication of the concentration of the analyte of interest in the sample applied to the sample portion of the device.

In such a device the sample portion, conjugate portion, diagnostic portion, and absorbent portion can be placed on a single solid support or backing material. This solid support or backing material may be flexible but is inert and provides sufficient support to maintain a capillary flow of the sample through the various portions that are of absorbent material.

The diagnostic portion of the lateral flow immunoassay device may be prepared using a membrane. Such diagnostic membrane can for example be selected from a nitrocellulose membrane, a polyvinylidene fluoride membrane, a nylon membrane that is optionally charge modified, and a polyethersulfone membrane. The diagnostic membrane further comprises an immobilized binder for the analyte. Such binder can be any molecule or bio-molecule with which the analyte of interacts so as to result in a binder-analyte complex that is immobilized onto the diagnostic membrane. Examples of such binders may be an antibody, antigen, protein, enzyme or part thereof, substrate or part thereof, peptide, DNA, or RNA.

An electrical sensor integrated in such LFIA device is preferably a printed electrical sensor. The electrical sensor can have one or more electrode pairs that are printed on the solid support of the LFIA device. Printing of the electrode pairs can be on any one of the sample portion, diagnostic portion, and/or absorbent portion of the solid support. Preferably, the electrodes are printed on the diagnostic portion of the device which contains the binder material for interaction with the analyte. Alternatively, the applied electrodes are non-printed electrodes.

The electrical sensor can be connected to a processing unit for computing one or more parameters of the sample. Such processing unit can comprise for example a CMOS unit for processing the data obtained, determining the value of the parameter of interest of the sample and computing the concentration of the analyte detected on the diagnostic portion/membrane of the LFIA device. Such parameter of the sample can for example be the flow rate of the sample across the diagnostic portion, the flow shape of the sample across the diagnostic portion, the temperature of the sample at the diagnostic portion, the pH of the sample at the diagnostic portion, and/or the ionic concentration of the sample at the diagnostic portion.

In addition, the processing unit preferably comprises a display to, for example, display the concentration of the analyte in the sample or any other measured or computed value of interest thereof. Further, the processing unit may be integrated in the LFIA device or the processing unit is connected to the LFIA device externally.

Figure 8:
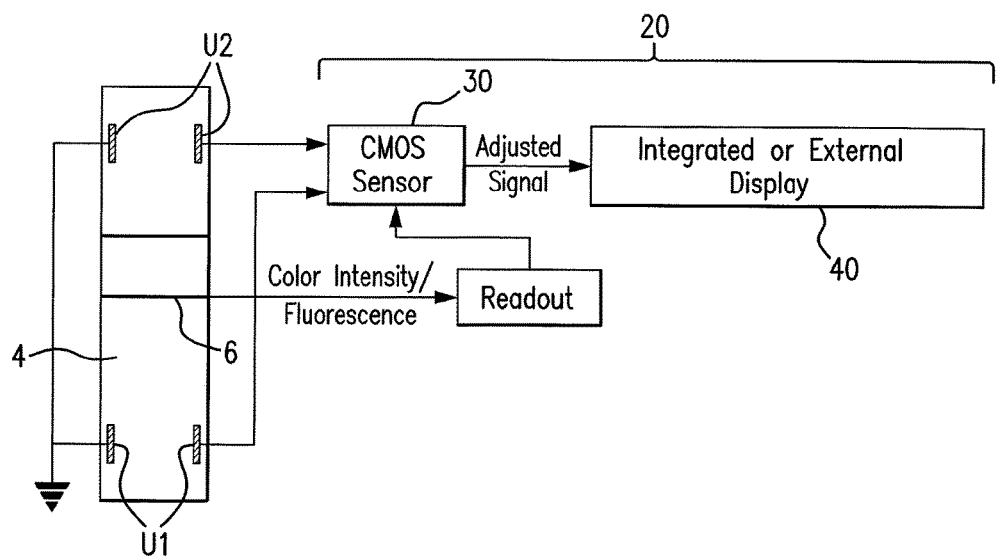
FIG. 8: Schematic representation of an integration of printed sensors in a lateral flow device. The intensity of the test line is adjusted by the data from the flow speed measurement which can be carried out by for example a CMOS sensor which transmits the signal to a display.

In one embodiment the LFIA device is provided with a flow speed sensor which comprises at least one, preferably at least two, electrode pairs which are integrated on the diagnostic part of the Lateral Flow Device. In one such embodiment two electrodes pairs are used, wherein one electrode pair is located in the flow direction before the test line on the diagnostic portion and the second pair of electrodes is located in the flow direction after the test lines of the diagnostic portion. A resistance measurement between corresponding electrodes provides information about the flow speed of the sample. When the sample crosses an electrode pair the resistance will drop due to the higher conductivity of the sample (fluid) compared to the conductivity of the dry test strip or diagnostic membrane. FIG. 8 shows an example of how such sensor system is included into a Lateral Flow Immunoassay device. For example the information from the color or fluorescence measurement can be adjusted by the information obtained from the flow speed measurement. The adjustment can for example be done by a CMOS-Sensor.

This combination of the label/signal readout for the analyte and flow rate of the sample compensates for example the effect of viscosity change.

In another embodiment the LFIA device is provided with a flow shape sensor. The flow shape sensor comprises electrode pairs that are integrated on the diagnostic part of the Lateral Flow Immunoassay device as shown for example in FIG. 3. Multiple electrode pairs are applied side-by-side to each other in an array perpendicular to the flow direction of the sample across the LFIA device. Depending on the desired resolution any amount of electrodes can be integrated on the diagnostic portion/membrane. The only limitation is the width of the diagnostic portion/membrane and the width of the electrode. When the flow shape is non-uniform several electrodes will get short-circuited earlier than others. For example, where there is a convex flow shape occurring on the diagnostic membrane the electrodes in the middle of the diagnostic portion/membrane will get short-circuited earlier than outside electrodes. These changes in the current signal can be measured. From compiling the data from the multiple electrode pairs the geometry of the flow shape can be determined, which then can be used to obtain important information about the signal intensity along the reaction lines.

In addition, a change in the temperature of a solution is correlated with the flow speed. Thus, in yet another embodiment the LFIA device is provided with a temperature sensor. A temperature sensor can get integrated on any membrane of the lateral flow device. By applying a defined structure of conductive material resistances in a defined range a temperature sensor can be integrated on the device. With changing temperature also the resistance of the (printed) electronic temperature sensor will change in a defined way Furthermore, in an embodiment having at least one, preferably at least two, temperature sensors and a heating element the flow rate can also be measured when the device is already wet such as in a device with continuous flow. As described herein a difference in the resistance in an electronic, here temperature, sensor provides a measurement of the flow time of the sample over the LFIA device from which the flow rate can be obtained. In such an embodiment, in a device with for example continuous flow, a heating element that is located before, in the flow direction, of the test line or diagnostic portion increases the temperature of the (sample) fluid. This can be measured by a temperature sensor. The flow of the (sample) fluid of increased temperature across the LFIA device, over a pre-determined distance, results in a difference that can be measured with such a temperature sensor. Form the determined flow time the flow speed/rate can be obtained. Similarly a combination of an array of such temperature sensors can be used to measure flow shape in such a device that is already wet. In such embodiment the LFIA device having at least one temperature sensor and a heating element comprises an array of temperature sensors located perpendicular to the flow direction in the LFIA device. As described, a change in the resistance measured by one of the temperature sensor of such an array of sensors provides a measurement of the flow time in one area defined by that one temperature sensor. The combination of the various flow times from the array of sensors provides a measurement of the flow shape of the sample across the LFIA device.

For any of the embodiments described a processing unit translates the values obtained from the electron pairs in the electrical sensors to a measured value of a parameter of the sample. After-pulse removal can be used in case to remove signal changes that may occur. Especially when there is very low sample volume available, the current signal will increase much slower to its maximum value than when there is a high amount of sample volume available (see FIG. 5). In a capillary flow device as a Lateral Flow Immunoassay device, the flow speed/rate of the sample across the diagnostic portion, comprising the binder for the analyte in a test line, is inversely related to the capillary flow time. The printed electrical sensors can determine the capillary flow time, the time needed to for the sample to travel a defined length through the absorbent material of the diagnostic portion. This capillary flow time is inversely related to the flow speed/rate of the sample across the LFIA device.

Further the effective concentration of an analyte in a sample is inversely related to the square of the change in flow rate. Accordingly, in adjusting for the flow speed/rate of the sample in determining the concentration of the analyte in a sample, a calibration algorithm may be used for accessing a look up table, which calibration is pre-determined based on the (absorbent) materials used for manufacturing the LFIA device and for a standard solution of a sample to be tested using such LFIA device.

The sensors and the actuators for the LFIA devices according to any of the embodiments can be prepared using printed electronics (e.g., conductive inks and temperature sensitive materials). As discussed they can be printed either directly on (for example) the nitrocellulose, on the backing material, or on a top layer that is attached to the device. Likewise, in an alternative embodiment, non-printed electrodes may be applied either directly onto the absorbent material (such as the nitrocellulose membrane), or through the backing material of the device. The interface to the electronic integrated circuits can be made by use of flex circuits or similar technologies.

In another embodiment there is provided a method of determining the concentration of an analyte in a sample comprising determining the analyte in the sample and a parameter of the sample in a lateral flow immunoassay device, wherein the lateral immunoassay device comprises a solid support including absorbent material for providing capillary flow comprising:

a) a sample portion for receiving a sample;
b) a conjugate portion comprising conjugate particulate material;
b) a diagnostic portion comprising a binder for the analyte;
c) an absorbent portion of absorbent material for providing capillary flow; and
d) at least one electrical sensor, wherein the sample portion, conjugate portion, diagnostic portion, and absorbent portion are in capillary flow communication, whereby the sample flows across the binder in the diagnostic portion to provide contact between the sample and the binder.

In FIG. 1 a solid support (1) comprising a sample portion (2), a conjugate portion (3), a diagnostic portion (4) and an absorbent portion (also referred to as a wick) (5) are shown. A sample (10) is applied to the sample portion (2) of the lateral flow immunoassay (LFIA) device. The sample flows by way of capillary flow towards the absorbent material (5) of the device. When passing through the conjugate portion (3) a label of particulate conjugate material interacts with the analyte forming a complex. Such complex continues to flow through capillary action across the diagnostic portion (4) of the LFIA device. A binder on a test line (6) interacts with the analyte of interest in the sample and immobilizes the analyte and conjugate particulate matter on the test line (6), the intensity of this label (conjugate particulate matter) is measured to determine the concentration of the analyte present in the sample.

Figure 2:
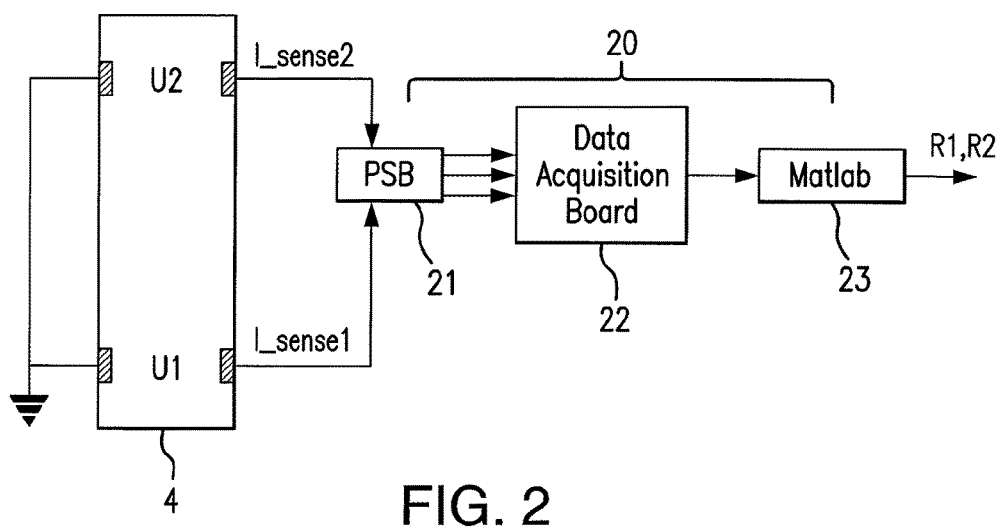
FIG. 2: A schematic representation of a setup for a flow speed measurement in a lateral flow immunoassay device.
Figure 3:
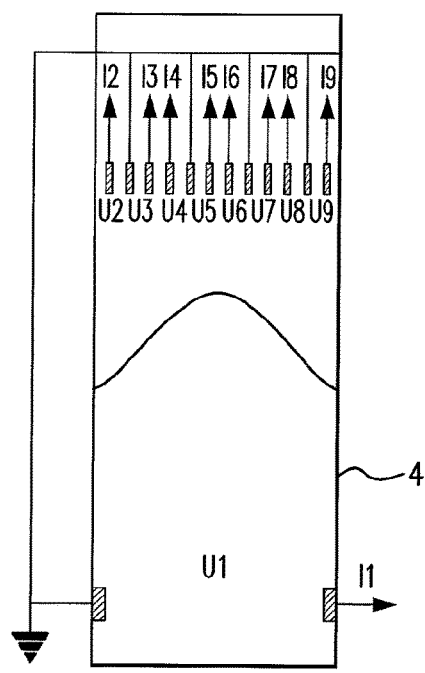
FIG. 3: A schematic representation of electrode pairs for flow shape sensors to determine non-uniform flow shape.
Figure 4A:
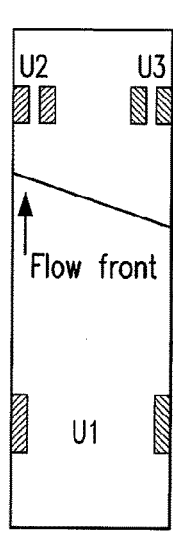
FIG. 4A: Showing measurements of a simple lateral flow immunoassay device for measuring the flow shape of a sample: non-uniform flow shape electrode (U2) is short-circuited prior to when flow shape electrode (U3) is short-circuited.

Electrical sensors with electrode pairs (U1 and U2) located on the solid support or parts thereof, such as the diagnostic portion (4) of the LFIA device, as in FIG. 2 can be used to determine a parameter of the sample such as the flow speed/rate of the sample across the diagnostic portion (4) of the LFIA device. The flow speed can be computed using a processing unit (20), which may consist of various components so as for example a printed control board (21), a data acquisition board (22), and a computer program (23). In FIG. 3, an array of multiple of such electrical sensors with electrode pairs (U2, U3, U4, U5, U7, U8, and U9) together with electrode pair (U1) are printed on a diagnostic portion (4) of the LFIA device for determining the flow shape of a sample across the diagnostic portion (4). Likewise the array of electrode pairs (U2 and U3) together with electrode pair (U3) in FIG. 4a is used to determine the flow shape of the sample across diagnostic portion (4).

In FIG. 7 printed electrode pairs (U1 and U2) can be integrated on portions of the solid support that is different than the diagnostic portion (4), such as in 7a where the electrode pair (U1) is printed onto the sample portion (2) and electrode pair (U2) is printed onto the absorbent portion (5). In the alternative, in FIG. 7b electrode pairs (U1 and U2) are printed on the backing or support (1) which is covered with the nitrocellulose membrane of the diagnostic portion (4). Electrode pairs (U1 and U2) can be accessed through the backing/support (1). In FIG. 7c another alternative is shown wherein the printed electrode pairs (U1 and U2) are printed in gaps in the nitrocellulose membrane of the diagnostic portion (4). Other variations of these may also be possible.

Integration of printed sensors in a lateral flow immunoassay device can be as in FIG. 8. Electrode pairs (U1 and U2) are printed on the diagnostic portion (4) of the lateral flow immunoassay device. The signal intensity from test line (6) such as color intensity or fluorescence intensity is measured and computed together with the measured values from electrode pairs (U1 and U2) by a processing unit (20) which can comprise a CMOS-sensor (30) and an integrated or external display (40).

EXAMPLES

Lateral Flow Immunoassay were prepared using the following materials. The diagnostic membrane (Hiflow Plus HFB 13504), a conjugate pad (G041 glass fiber conjugate pad) and the absorbent pad (C083 cellulose Absorbent) were all from Millipore. The sample pad (CF5) was from Whatman. Preparation of the conjugate pad was done using the protocol by S. Wang et al. "Development of a colloidal gold-based lateral flow immunoassay for the rapid simultaneous detection of zearalenone and deoxynivalenol", Anal. Bioanal. Chemistry (2007). The protocol to treat the nitrocellulose diagnostic membrane was described in "Lateral Flow Tests" Technote, Bangs Laboratories. Inc. (2008).

Example 1 (Flow Speed Sensor)

Conductive silver ink (DuPont 4929N) was applied to the treated nitrocellulose membrane using an art brush. The electrodes were connected to a printed circuit board (PCB) (see FIG. 2). A fixed voltage of v=1V was applied between each electrode pair and the corresponding current was measured by an instrumentation amplifier on the PCB. A Data Acquisition Board from National Instruments was used as the interface between the PCB and the computer (Matlab-Mathworks).

Two different solutions with different viscosities (PBS and Glycerol diluted in PBS 1:3) were applied to the sample pad of the LFIA. A solution of 1:3 PBS Glycerol decreases the flow speed to around ¼ of the flow speed measured with pure PBS solution.

Figure 5A:
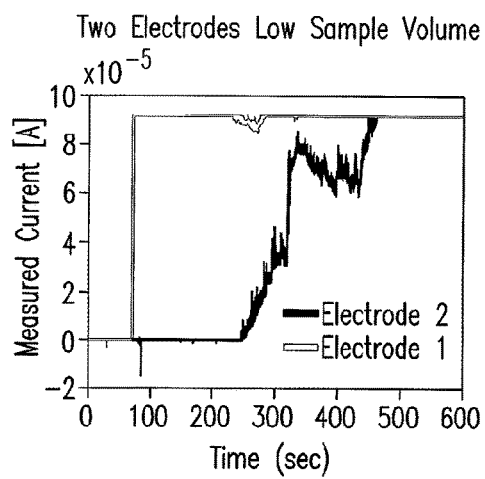
FIG. 5A: Graph showing measurements of different flow speeds due to different amounts of sample volume: 500 µl of PBS (flow front moves very slowly).
Figure 5B:
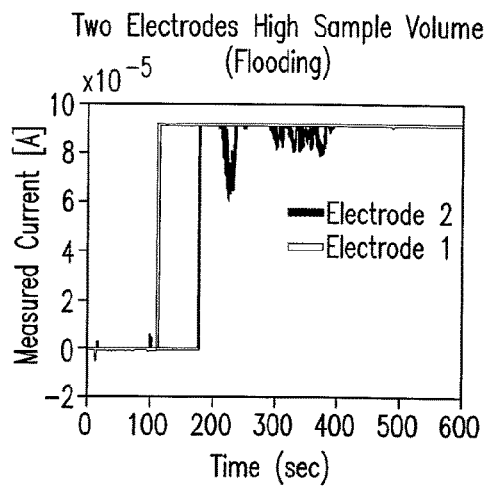
FIG. 5B: Graph showing measurements of different flow speeds due to different amounts of sample volume: 1000 µl of PBS (membrane is flooded).
Figure 6:
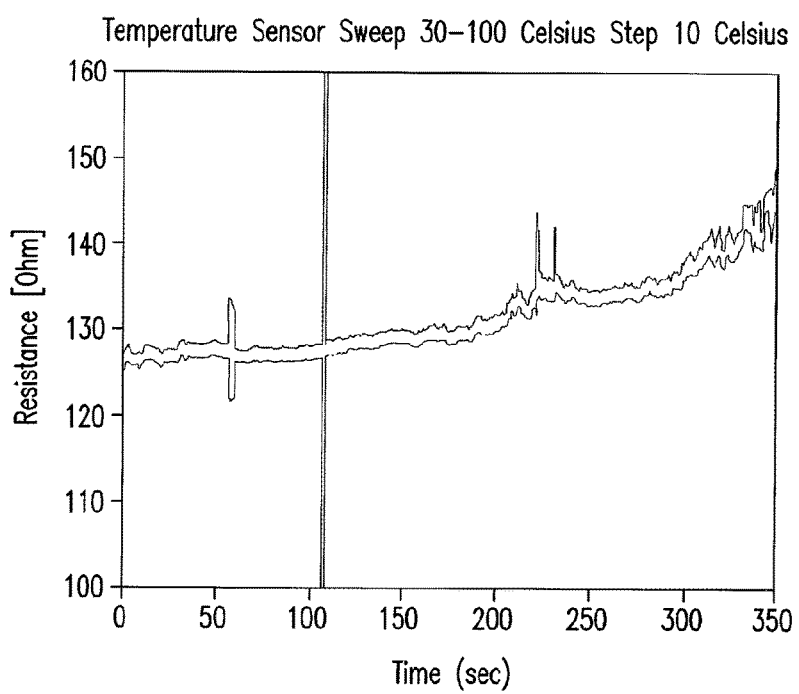
FIG. 6: Graph showing temperature sensing. Temperature sweep started at 30° C. to 100° C. on a hotplate.

To show the influence of wrong sample application on the flow speed a very low sample volume (500 µl) and a high sample volume (1000 µl) were compared with each other. The flow front of the low volume sample moved very slowly along the diagnostic membrane (v≈3 cm/min) where the flow front of the high volume sample moved very fast (v≈1 cm/min) and even flooded the membrane. FIG. 5 shows the results of the flow speed measurement.

Example 2 (Flow Shape Sensor)

Figure 4B:
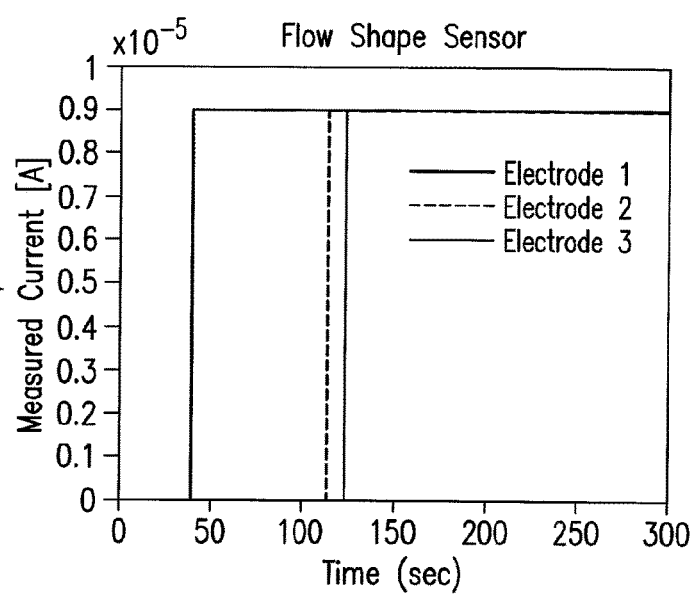
FIG. 4B: Showing measurements of a simple lateral flow immunoassay device for measuring the flow shape of a sample: graph showing the measured current signal (with after-pulse removal).

Conductive silver ink (DuPont 4292N) was applied to the treated nitrocellulose membrane using an art brush. The setup that was used is shown in FIG. 4a wherein multiple electrode pairs were applied to the treated nitrocellulose membrane. A non-uniform flow shape was created on purpose by applying a much larger amount of sample volume on the left side of the sample pad. The flow shape that was created looked similar to the one indicated in FIG. 4a. The results (after pulse removal) are shown in FIG. 4b. Due to the non-uniform flow front electrode 2 got shorted prior to electrode 3 being shorted.

Example 3 (Temperature Sensor)

Conductive platinum ink (DuPont BQ321) was printed on the sample pad of the LFIA. The resistance was set to 110Ω at room temperature. The temperature of a hotplate was slowly increased to 100° C. An increase of the resistance was observed that was similar to a standard platinum Pt100 temperature sensor.

The invention claimed is:

1. A method comprising:
   determining a parameter of a sample in a lateral flow immunoassay device, and
   determining a concentration of an analyte in the sample based on the determined parameter;
   wherein:
   the lateral immunoassay device comprises:
   a) a solid support;
   b) a sample portion for receiving the sample;
   c) a conjugate portion comprising conjugate particulate material;
   d) a diagnostic portion comprising a binder for the analyte in the sample;
   e) an absorbent portion of absorbent material for providing capillary flow; and
   f) at least one electrical sensor; and
   the sample portion, conjugate portion, diagnostic portion, and absorbent portion are in capillary flow communication, whereby the sample flows across the binder in the diagnostic portion to provide contact between the sample and the binder;
   wherein the at least one electrical sensor is connected to a processing unit that is configured to compute:
   the parameter of the sample at the diagnostic portion using a signal provided by the at least one electrical sensor; and
   the concentration of the analyte using (a) a signal generated from a binding of the binder and the analyte in the sample and (b) the parameter of the sample; and
   wherein the at least one electrical sensor and the binder for the analyte are both placed on one side of the solid support, the at least one electrical sensor being located on a portion of the solid support different from the binder for the analyte.

2. The method of claim 1, wherein the processing unit comprises a display.

3. The method of claim 1, wherein the parameter includes at least one of a flow rate of the sample across the diagnostic portion, a flow shape of the sample across the diagnostic portion, a temperature of the sample at the diagnostic portion, a pH of the sample at the diagnostic portion, and an ionic concentration of the sample at the diagnostic portion.

4. The method of claim 1, wherein:
   the sample:
   flows through the conjugate portion, whereby the analyte binds to and forms a complex with the conjugate particulate material; and
   flows through the diagnostic portion, whereby the binder interacts with the analyte and immobilizes the analyte and conjugate particulate material complex;
   the conjugate particulate material bound to the analyte generates a signal;
   the method further comprises measuring a signal intensity from the conjugate particulate material bound to the analyte at the diagnostic portion;
   the determining of the parameter includes measuring the parameter at the diagnostic portion; and
   the determination of the concentration of the analyte is further based on the measured signal intensity.

5. The method of claim 4, wherein the parameter of the sample affects the signal intensity from the bound analyte-conjugate particular material complex.

6. The method of claim 5, wherein the parameter is the flow rate of the sample across the diagnostic portion, the flow shape of the sample across the diagnostic portion, the temperature of the sample at the diagnostic portion, the pH of the sample at the diagnostic portion, and/or the ionic concentration of the sample at the diagnostic portion.

7. The method of claim 1, wherein the processing unit is also connected to a display and is configured to display the determined analyte concentration on the display.

8. The method of claim 1, wherein the processing unit is connected to the lateral flow immunoassay device externally.

9. The method of claim 1, wherein the processing unit is integrated into the lateral flow immunoassay device.

10. The method of claim 1, wherein the at least one electrical sensor is positioned downstream of the binder in a capillary flow direction.

11. The method of claim 1, wherein the at least one electrical sensor is printed or applied directly on the diagnostic portion.

12. The method of claim 11, wherein the at least one electrical sensor comprises at least one electrode pair.

13. The method of claim 11, wherein the at least one electrical sensor comprises two electrode pairs to determine a flow rate of the sample across the diagnostic portion.

14. The method of claim 13, wherein, when determining the concentration of the analyte, a calibration algorithm is used to access a look up table.

15. The method of claim 11, wherein the at least one electrical sensor comprises a series of multiple electrode pairs arranged side-by-side across the flow path of the sample to determine a flow shape of the sample across the diagnostic portion.

16. The method of claim 11, wherein the at least one electrical sensor comprises a defined structure of conductive material resistances in a define range for determining a temperature of the sample flowing across the diagnostic portion.

17. The method of claim 11, wherein the at least one electrical sensor comprises at least one temperature sensor, and the device further comprises a heating element located, in the flow direction of the sample, before the at least one temperature sensor.

18. The method of claim 11, wherein the at least one electrical sensor comprises a series of multiple temperature sensors arranged side-by-side across the flow path of the sample, and the device further comprises a heating element located, in the flow direction of the sample, before the at least one temperature sensor, to determine a flow shape of the sample across the diagnostic portion of the lateral flow device.

* * * * *